United States Patent
Li et al.

(10) Patent No.: US 9,062,161 B2
(45) Date of Patent: Jun. 23, 2015

(54) METHOD FOR PREPARING POLYMETHYLENE POLYPHENYL POLYCARBAMATE

(75) Inventors: Huiquan Li, Beijing (CN); Haitao Liu, Beijing (CN); Jiaqiang Chen, Beijing (CN); Kaihua Zhang, Beijing (CN); Yan Cao, Beijing (CN)

(73) Assignee: Institute of Process Engineering, Chinese Academy of Sciences, Beijing (CN)

( * ) Notice: Subject to any disclaimer, the term of this patent is extended or adjusted under 35 U.S.C. 154(b) by 0 days.

(21) Appl. No.: 14/356,656

(22) PCT Filed: Nov. 8, 2011

(86) PCT No.: PCT/CN2011/081909
§ 371 (c)(1),
(2), (4) Date: May 30, 2014

(87) PCT Pub. No.: WO2013/067679
PCT Pub. Date: May 16, 2013

(65) Prior Publication Data
US 2014/0316100 A1    Oct. 23, 2014

(51) Int. Cl.
| C08G 69/44 | (2006.01) |
| C08G 71/04 | (2006.01) |
| C08G 12/04 | (2006.01) |
| C07C 269/06 | (2006.01) |
| C08L 77/00 | (2006.01) |

(52) U.S. Cl.
CPC ............. *C08G 71/04* (2013.01); *C08G 12/04* (2013.01); *C07C 269/06* (2013.01)

(58) Field of Classification Search
USPC ............. 524/602; 560/24, 25, 345; 528/165
See application file for complete search history.

(56) References Cited

U.S. PATENT DOCUMENTS 5,384,424 A    1/1995    Oh et al.

FOREIGN PATENT DOCUMENTS

| CN | 101440048 | 5/2009 |
| DE | 206 669 | 2/1984 |
| EP | 0123412 A1 | 10/1984 |
| JP | 56167656 | 12/1981 |
| JP | 58062151 | 4/1983 |
| JP | S5929651 A | 2/1984 |
| JP | H02108658 A | 4/1990 |
| JP | 04202172 | 7/1992 |

OTHER PUBLICATIONS

Gongying Wang, Synthesis of Methylene Diphenyl Dicarbamate Over Mixed Acid Catalyst, *Chemical Engineering of Natural Gas*, 2004, 29(2), pp. 33-36. (Translation of abstract only).
Wang, Fuqiang et al., Synthesis of Methyl Methylene Di(Phenyl Carbamate) Catalyzed by Sulfuric Acid With Chloride as the Promoter, *Industrial Catalysis*, Aug. 2006, vol. 14, No. 8, pp. 44-47. (Translation of abstract only).
Geng, Yanlou et al., Synthesis of 4,4'-MDC in the Presence of Sulfonic Acid-Functionalized Ionic Liquids, *Chinese Journal of Chemical Engineering*, 2009, 17(5), pp. 756-760.
Hu, Li-yan et al., Syntheses of 4,4'-MDC in the Presence of [emim]$BF_4$ Ionic Liquid Modified With $H^+$, *Journal of Chemical Engineering of Chinese Universities*, 2007, 21(3); pp. 467-470.

*Primary Examiner* — Terressa Boykin
(74) *Attorney, Agent, or Firm* — McDermott Will & Emery LLP

(57) ABSTRACT

A method for preparing polymethylene polyphenyl polycarbamate is provided. The method includes dissolving phenylcarbamate in a water-immiscible organic solvent to form a solution A, formulating an aqueous acid catalyst solution to form a solution B, forming a reaction system comprising an organic phase and an aqueous phase by firstly adding a methylating reagent to the solution B and then mixing the solution A and the solution B, wherein the organic phase comprises phenylcarbamate and the aqueous phase comprises the acid catalyst and the methylating reagent. The method further includes reacting the reaction system under stirring at a reaction temperature of 30° C. to 200° C. and a reaction pressure of 0.05 MPa to 5 MPa to produce a polymethylene polyphenyl polycarbamate product mixture dissolved in the organic phase, and separating the polymethylene polyphenyl polycarbamate product mixture by allowing the organic phase and the aqueous phase to stand still and stratify.

17 Claims, No Drawings

METHOD FOR PREPARING POLYMETHYLENE POLYPHENYL POLYCARBAMATE

CROSS REFERENCE TO RELATED APPLICATIONS

This application is a National Phase Application filed under 35 USC 371 of International Application No. PCT/CN2011/081909, filed on Nov. 8, 2011, the entire content of which is hereby incorporated by reference in its entirety.

TECHNICAL FIELD

The present disclosure relates to a method for preparing polymethylene polyphenyl polycarbamate and pertains to the technical field of producing a polymer compound.

BACKGROUND

The isocyanate products have a value of widespread industrial application and are mainly classified into aliphatic isocyanates and aromatic isocyanates which can produce various polyurethane products by polymerization. In these products, the aromatic isocyanates have the greatest market demand. The aromatic polyisocyanates are very important raw materials and have been widely applied to the fields of synthetic leathers, fibers, coatings, plastics and so on. Recently, with the increased market demands of the domestic automobiles, leather production and construction industry, the demand of the aromatic polyisocyanates has been also rapidly expanded.

The approach of synthesizing the aromatic isocyanates can be achieved by various technical routes. However, the method currently used for the industrial production is mainly a phosgene process due to the economy thereof. Since the phosgene process has high toxicity and severe pollution due to use of hypertoxic phosgene raw material and is thus hazardous to the ambient ecology and environment, it has an extremely high requirement for the industrial mass production, which severely limits the enlargement of the production of the aromatic polyisocyanates and the widespread application of the downstream products. Therefore, there is an urgent demand for green processes of producing the aromatic isocyanate products. Moreover, the process of producing the aromatic polyisocyanates through the pyrogenation of polymethylene polyphenyl aromatic carbamate is most likely to be industrialized and is desirable to produce the aromatic polyisocyanate in place of the phosgene process.

In the green processes of synthesizing the aromatic polyisocyanates, the efficient synthesis of polymethylene polyphenyl aromatic carbamate is one of the critical determining factors for achieving the industrialization of the process. Polymethylene polyphenyl aromatic carbamate can be synthesized through various technical routes. In these technical routes, the production of polymethylene polyphenyl polycarbamate through the condensation of monophenyl carbamate and methylating reagent has been mostly investigated. It is generally a relatively complicated process to produce polymethylene polyphenyl polycarbamate through the condensation of monophenyl carbamate and methylating reagent. The resulting polymethylene polyphenyl polycarbamate is present in the form of various isomers and the product is a mixture of carbamates having various benzene ring numbers. In conventional condensation reaction processes, it is often necessary to use different solvents as the reaction medium according to the requirement of the reaction catalyst. The used catalyst is mainly classified into a liquid protonic acid and the liquid protonic acid catalyst mainly comprises a strong acid such as an inorganic acid (sulfuric acid, hydrochloric acid, hydrofluoric acid etc.) and an organic acid (formic acid, acetic acid, butyric acid etc.).

In the U.S. Pat. No. 4,307,029 (1981), Takeuchi et al. have reported a technical route for synthesizing polymethylene polycarbamate through the condensation of phenylcarbamate with formaldehyde or derivative thereof in an organic solvent under the catalyzation of a Lewis acid and a protonic acid, followed by the formation of the corresponding polyisocyanate mixture through pyrogenation. However, because the composition of the condensed product is complicated and the pyrogenating temperature is higher, the composition of the final product is more complicated, and the subsequent separation in the scale-up process is extremely complicated, bringing about the difficulty of industrialization thereof.

In the patent JP 01135758, Takeshita et al. have reported that the technical route for synthesizing methylene diphenyl di(ethyl carbamate) through the condensation of ethyl phenylcarbamate with formaldehyde under the catalyzation of sulfuric acid can achieve a conversion of ethyl phenylcarbamate of 98.4% and a yield of the product of 73%.

In the patent DD206669-A, Jungnickel has used 20% of hydrochloric acid as the catalyst and solvent and investigated the reaction for producing methylene diphenyl di(methyl carbamate) through the condensation of methyl phenylcarbamate and formaldehyde, wherein the selectivity of 4,4'-methylene diphenyl di(methyl carbamate) is 72% and the selectivity of 2,4'-methylene diphenyl di(methyl carbamate) is 7%.

In the patent JP 04202172, Muzakami has proposed that strong acids such as $HCO_2H$, $H_3PO_4$ and $H_2SO_4$ are formulated into an aqueous mixed acid solution as the catalyst and solvent for the condensation of carbamate and formaldehyde, wherein the conversion of carbamate is 92% and the selectivity of the product is 88%.

Prof. Gongying Wang in the Chengdu Institute of Organic Chemistry of the Chinese Academy of Science has successively reported (Chemical Engineering of Natural Gas, 2004, volume (vol.) 29(2), pages (pgs.) 33-36; and Industrial Catalysis, 2006, vol. 14(8), pgs. 44-47) that methylene diphenyl di(methyl carbamate) is synthesized through the condensation in a system of a mixed acid and of sulfuric acid, wherein the reaction of producing methylene diphenyl di(methyl carbamate) through the condensation of methyl phenylcarbamate and formaldehyde solution (or trioxymethylene) in the presence of 30% of the mixed acid catalyst produces the following results: when formaldehyde is used as the methylating reagent, the yield of the product is 89.47%, and when trioxymethylene is used as the methylating reagent, the yield of the product is 75.81%. The reaction of producing methylene diphenyl di(methyl carbamate) through the condensation of methyl phenylcarbamate and formaldehyde by adding hydrochloride salt promoter to the system on the basis of the sulfuric acid catalyst has been further investigated and it has been found that the conversion of methyl phenylcarbamate is 96% and the yield of 4,4'-methylene diphenyl di(methyl carbamate) can be 76.7%, but the introduction of chloride ions to the reaction system will affect the usability of the product in the subsequent application.

Prof. Yanji Wang et al. have reported the reaction of catalytically synthesizing methylene diphenyl di(methyl carbamate) from methyl phenylcarbamate and formaldehyde in a system of a protonic acid-acidified 1-ethyl-3-methylimidazolium tetrafluoroborate ([emim]$BF_4$) ionic liquid (Journal of Chemical Engineering of Chinese Universities, 2007, vol. 21(3), pgs. 467-470) and of a sulfonic acid-functionalized ionic liquid (Chinese Journal of Chemical Engineering, 2009, vol. 17(05), pgs. 756-760). However, the yield of the product is less than 75%.

In the above patents and literatures, the condensation of phenylcarbamate has been investigated mainly by selecting and using the liquid and solid acid catalysts in a water-phase system, and the inexpensive and easily available formalin (aqueous formaldehyde solution) has been used as the methylating reagent during the production so that the production cost is low. However, there are the technical difficulties of corrosion of apparatus, the great amount of acid liquid used and the complicated post treatment processes such as the separation of the acid liquid from the solid polycyclic carbamate product in the production. Moreover, it is extremely difficult to wash off the acid liquid entrained by the solid product, which limits the industrial scale-up and application thereof.

Monica Distaso et al. (JP 58062151, JP 56167656 and US 1981-05-19) have used $Sc(OTf)_3$ and $La(OTf)_3$ ($OTf=O_3SCF_3$) as the catalyst and investigated the reaction where phenyl methyl carbonate is used as the carbonylating agent of the aromatic diamine. The methoxycarbonylating reaction of MDA and phenyl methyl carbonate in tetrahydrofuran organic solvent is markedly improved, wherein the overall yield of carbamate is approximately 80% and the selectivity is as high as 94%. However, the stabilization, separation, recycle and reuse of the above catalyst are technically problematic, which limits the further industrial application thereof. In the patent CN 101440 048, by introducing the mixed solvent system of acetic acid and water, the applicant has improved the yield of the product from the condensation of methyl phenylcarbamate and formaldehyde at a certain degree and relieved the problem of entraining liquid acid catalyst in the solid product. However, it has not disclosed that the presence of a proper amount of solvent allows the reaction to occur in the uniform liquid phase system and the crystallization of the solid product during the reaction to be completely avoided such that the technical difficulty of separating the product from the acid catalyst and recycle and reuse the product can be fundamentally solved.

In the above technical routes of synthesizing polymethylene polyphenyl polycarbamate, the reaction system has a complicated multiphasic phenomenon where the aqueous phase, oil phase and solid phase are co-existed and the solid phase product entrains the phenylcarbamate oil phase raw material and the catalyst, which results in the technical difficulty of complicated subsequent product separation and purification.

SUMMARY

Disclosed herein is a method for preparing polymethylene polyphenyl polycarbamate.

In one aspect, a method for preparing polymethylene polyphenyl polycarbamate which is carried out through the condensation of phenylcarbamate with a methylating reagent under the catalyzation of a phase transfer acid catalyst. The method includes dissolving phenylcarbamate in a water-immiscible organic solvent to form a solution A, formulating an aqueous acid catalyst solution to form a solution B, forming a reaction system comprising an organic phase and an aqueous phase by firstly adding a methylating reagent to the solution B and then mixing the solution A and the solution B, or by adding the methylating reagent at the same time of mixing the solution A and the solution B or after mixing the solution A and the solution B, wherein the organic phase comprises phenylcarbamate and the aqueous phase comprises the acid catalyst and the methylating reagent. The method further includes reacting the reaction system under stirring at a reaction temperature of 30° C. to 200° C. and a reaction pressure of 0.05 megapascal (MPa) to 5 MPa to produce a polymethylene polyphenyl polycarbamate product mixture dissolved in the organic phase, and separating the polymethylene polyphenyl polycarbamate product mixture by allowing the organic phase and the aqueous phase to stand still and stratify.

In another aspect, the method further includes crystallizing the polymethylene polyphenyl polycarbamate product mixture by decreasing the temperature thereof so as to separate methylene diphenyl dicarbamate therefrom.

In another aspect, the method further includes selecting the organic solvent from linear alkylanes, cyclic alkanes, naphthenic oils, halogenated hydrocarbons, aromatic hydrocarbons, esters and a combination thereof.

These as well as other aspects, advantages, and alternatives will become apparent to those of ordinary skill in the art by reading the following detailed description. Further, it should be understood that the disclosure provided in this summary section and elsewhere in this document is intended to discuss the embodiments by way of example only and not by way of limitation.

DESCRIPTION OF THE DISCLOSURE

In order to solve the above problem, the present disclosure provides a simple, green and highly efficient synthesis method for preparing polymethylene polyphenyl polycarbamate through the condensation of phenylcarbamate with a methylating reagent under the catalyzation of a phase transfer acid catalyst. This method can produce polymethylene polyphenyl polycarbamate at high selectivity and yield and can achieve the easy separation of the product and avoid the problem of entraining the raw material, phenylcarbamate, in the oil phase and the catalyst by the solid phase product. Specifically, a biphasic system of an aqueous phase and an organic phase is introduced to the reaction of producing polymethylene polyphenyl polycarbamate through the condensation of phenylcarbamate with a methylating reagent in the presence of an acid catalyst, so as to achieve the uniform liquid phase synthesis of polymethylene polyphenyl polycarbamate under stirring.

The method for preparing polymethylene polyphenyl polycarbamate through the condensation of phenylcarbamate with a methylating reagent under the catalyzation of a phase transfer acid catalyst is illustrated by the following reaction scheme:

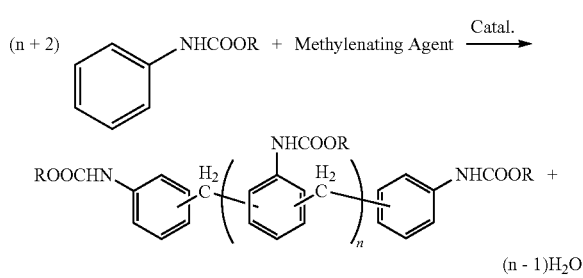

wherein n may be an integer of 0 to 18, R may be a hydrocarbyl group containing 1 to 20 carbon atoms, for example, a saturated alkyl group containing 1 to 20 carbon atoms, and preferably, a C1-C4 alkyl group, an aromatic hydrocarbyl group and an unsaturated alkenyl group and the like, and the corresponding polymethylene polyphenyl polycarbamate has a number of benzene ring in the range of 2 to 20 and preferably 2 to 10 and comprises polymethylene polyphenyl polycarbamic acid alkyl ester, polymethylene polyphenyl polycarbamic acid aryl ester, polymethylene polyphenyl polycarbamic acid alkenyl ester and the like and further, the isomers thereof, with the product wherein n=0 or 1 being the main product.

Specifically, the present disclosure provides a method for preparing polymethylene polyphenyl polycarbamate which is carried out through the condensation of phenylcarbamate with a methylating reagent under the catalyzation of a phase transfer acid catalyst, comprising the steps of:

a. dissolving phenylcarbamate in a water-immiscible organic solvent to form a solution A;

b. formulating an aqueous acid catalyst solution to form a solution B;

c. forming a reaction system comprising an organic phase and an aqueous phase by firstly adding a methylating reagent to the solution B and then mixing the solution A and the solution B, or by adding the methylating reagent at the same time of mixing the solution A and the solution B or after mixing the solution A and the solution B, wherein the organic phase comprises phenylcarbamate and the aqueous phase comprises the acid catalyst and the methylating reagent;

d. reacting the reaction system under stirring at a reaction temperature of 30° C. to 200° C. and a reaction pressure of 0.05 MPa to 5 MPa to produce a polymethylene polyphenyl polycarbamate product mixture dissolved in the organic phase; and e. separating the polymethylene polyphenyl polycarbamate product mixture by allowing the organic phase and the aqueous phase to stand still and stratify.

In an embodiment of the method of the present disclosure, the method further comprises the step of:

f. crystallizing the polymethylene polyphenyl polycarbamate product mixture by decreasing the temperature thereof so as to separate methylene diphenyl dicarbamate therefrom.

The oil phase can be separated from the aqueous phase by an oil-water separator and the oil phase, the unreacted methylating reagent and aqueous acid catalyst solution can be recycled and reused after separating the products by the temperature-decreasing crystallization. The resulting solid polymethylene polyphenyl polycarbamate product may be subjected to the purifying treatment process such as washing with a solvent and recrystallization to obtain a highly pure product according to the particular application requirements, or may be directly used. The washing solvent comprises a solvent in which polymethylene polyphenyl polycarbamate has a low solubility, for example, a lower alcohol (C1-C6), acetone, chlorobenzene, dichlorobenzene and the like.

In an embodiment of the method of the present disclosure, the organic solvent in the step a is selected from linear alkylanes (for example, n-pentane etc.), cyclic alkanes (for example, cyclohexane, decahydronaphthalene etc.), naphthenic oils, halogenated hydrocarbons (for example, dichloroethane etc.), aromatic hydrocarbons (for example, benzene, toluene, xylene, o-diethylbenzene, o-dimethylbenzene, chlorobenzene, o-dichlorobenzene, p-dichlorobenzene, monochlorobiphenyl, diphenylmethane etc.), esters (for example, diisooctyl sebacate, phthalic acid esters such as dialkyl terephthalate, diethyl phthalate etc.) and a combination thereof.

In an embodiment of the method of the present disclosure, in the step a, the mass concentration of phenylcarbamate in the solution A is 1% to 90% and preferably in the range of 20% to 50%.

In an embodiment of the method of the present disclosure, the aqueous acid catalyst solution in the step b may be a liquid inorganic acid (for example, sulfuric acid, nitric acid, hydrochloric acid, phosphoric acid, boric acid), a liquid organic acid (for example, formic acid, acetic acid, butyric acid) or a mixture thereof.

In an embodiment of the method of the present disclosure, the mass fraction of the acid catalyst in the aqueous acid catalyst solution is 5% to 80%, and preferably in the range of 20% to 60%.

In an embodiment of the method of the present disclosure, a promoter is added to the aqueous acid catalyst solution in the step b.

In an embodiment of the method of the present disclosure, the promoter may be one of metal salts from the group IB, IIB, IIIA or VA or a combination of two thereof, or may be an inorganic chloride such as sodium chloride and copper chloride, an oxide such as dibutyl tin oxide or nanometer zinc oxide, and the mass concentration of the promoter in the aqueous acid catalyst solution is 0.01% to 20% and preferably 2% to 8%.

In an embodiment of the method of the present disclosure, the methylating reagent in the step c is selected from formaldehyde, paraformaldehyde (for example, trioxymethylene) and a combination thereof. The methylating reagent may further be trioxane, dioxacyclooxane, dioxane, dithiane, or oxathiane.

In an embodiment of the method of the present disclosure, the reaction in the step d is conducted in a reactor selected from one of a tubular reactor, a tower reactor, a tank reactor, a jet reactor, a moving bed reactor and a super-gravity reactor or a combination of two thereof.

In an embodiment of the method of the present disclosure, a volume ratio of the organic phase to the aqueous phase in the biphasic reaction system is between 0.1 and 100 and preferably between 0.5 and 10.

In an embodiment of the method of the present disclosure, a molar ratio of the methylating reagent to phenylcarbamate in the biphasic reaction system is 0.05 to 10.0 and preferably 0.25 to 2.0.

In an embodiment of the method of the present disclosure, the reaction temperature is preferably 60° C. to 120° C., and the reaction pressure is preferably 0.1 MPa to 1.0 MPa. The reaction temperature and pressure are mainly determined by the type of a solvent.

In an embodiment of the method of the present disclosure, the reaction time is 1 minute to 480 minutes and preferably in the range of 30 minutes to 120 minutes.

In an embodiment of the method of the present disclosure, the temperature for the temperature-decreasing crystallization is 20° C. to 100° C. and preferably in the range of 50° C. to 80° C. The reaction temperature for the crystallization separation is mainly determined by the solubility of the product in the solvent and the operation pressure of the crystallizer.

In an embodiment of the method of the present disclosure, the mass concentration of the polymethylene polyphenyl polycarbamate product mixture in the organic phase is 1% to 80% and preferably 5% to 40%.

The method of the present disclosure is unique in the design of synthetic route and simple in the operation and can reduce the energy consumption of the process while effectively improving the utilization rate of phenylcarbamate. Specifically, in the present disclosure, the highly efficient phase transfer catalytic synthesis has been achieved by introducing a two phase system of an aqueous phase and an organic phase, and the reaction process is carried out in a uniform liquid phase consisting of an oil phase and an aqueous phase. A yield of polymethylene polyphenyl aromatic carbamate product of 95% or more can be achieved under optimal reaction conditions. The products in the oil phase can be highly efficiently separated from the methylating reagent and the catalyst in the aqueous phase simply by the separation of the oil phase and the aqueous phase after the reaction is complete. The new route has the following advantages: (1) the phenylcarbamate raw material is dissolved in the organic phase and the methylating reagent is dissolved in the aqueous phase such that the progress of the reaction can be flexibly controlled by controlling the charge ratio of the two phases and the reaction time, and the composition of the polymethylene polyphenyl polycarbamate product can be highly effectively controlled by simple change of the conditions of the synthetic process; (2) the synthesized polymethylene polyphenyl polycarbamate product can be quickly transferred into the organic phase such that the reaction equilibrium is positively shifted so as to improve the yield of the reaction product; (3) the adverse factor of affecting the mass transfer by polymethylene polyphenyl polycarbamate precipitated in the aqueous phase in the form of solid during the synthesis in aqueous phase is eliminated and the technical difficulty of solid-liquid separation in the process of synthesizing polymethylene polyphenyl polycarbamate is avoided, and where the polymethylene polyphenyl polycarbamate product can be obtained by separating the oil phase from the aqueous phase using an oil-water separator, and the highly pure methylene diphenyl dicarbamate can be obtained by the temperature-decreasing crystallization of the separated oil phase; (4) the unreacted methylating reagent and acid catalyst are transferred into the aqueous phase after the reaction is complete such that the product can be highly efficiently separated from the raw materials and the catalyst by simple separation of the oil phase and aqueous phase, and the separated acid catalyst and unreacted methylating reagent in the aqueous phase can be directly recycled and reused; and (5) the synthetic route has the technical advantages of simple process, mild operation conditions, highly efficient product control and easy continuous production.

The present disclosure has solved the problems of the prior arts, and can achieve a very high yield close to 100% and obtain very pure methylene diphenyl dicarbamate with a purity of 95% or more by separation. The new method of producing polymethylene polyphenyl polycarbamate through the condensation of phenylcarbamate with a methylating reagent under the catalyzation of a phase transfer acid catalyst has an improvement of selectivity to the target product of 15% to 40% as compared with conventional methods, and all of the reactants and solvents can be recycled and reused, and the conversion of phenylcarbamate recycled and cumulated in the process is greater than 98%. As a whole, this new process is a green, highly efficient and low-energy-consumption technical route. In addition, the present disclosure allows the simple separation of used acid catalyst and oil phase and thus has very good recyclability and reusability in addition to very high selectivity and yield.

EXAMPLES FOR CARRYING OUT THE PRESENT DISCLOSURE

Hereafter, the examples of the method provided by the present disclosure are further illustrated, but the present disclosure is not limited thereto in any way.

Example 1

100.0 grams (g) of methyl phenylcarbamate was weighted and dissolved in 500 milliliters (ml) of toluene and they were fully mixed in a 1 litter (L) flask. A 1000 ml of an aqueous hydrochloric acid solution with a concentration of 30% was formulated in a 1 L beaker, and it was fully mixed with 30 g of trioxymethylene methylating reagent. The above solutions were mixed under stirring in a 2 L three-necked beaker, heated to 90° C. in an oil bath and reacted at the normal pressure for 8 hrs. After the reaction was complete, the stirring was stopped and the solution was allowed to stand still and stratify for the oil water separation. Each of the oil phase and the aqueous phase was then sampled at a certain mass for high performance liquid chromatography analysis. As a result, the conversion of methyl phenylcarbamate was 61.1% and the selectivity of polymethylene polyphenyl polycarbamate was 98.0%, wherein the selectivity of methylene diphenyl di(methyl carbamate) was 80.6%, the selectivity of trimethylene polyphenyl poly(methyl carbamate) was 16.2%, and the selectivity of tetramethylene polyphenyl poly(methyl carbamate) was 1.1%. The temperature of the oil phase product was decreased to 40° C., and 94% of dimethylene polyphenyl poly(methyl carbamate) (i.e., methylene diphenyl di(methyl carbamate)) was separated in the form of crystal and filtered to obtain the target product at a purity of 95% or more.

Example 2

30.2 g of butyl phenylcarbamate was weighted and dissolved in 100 ml of chlorobenzene (110 g). The solution was then poured into a 500 ml three-necked flask. The three-necked flask was then further charged with 200 ml of 40% phosphoric acid and placed into an oil bath to be heated to 80° C. Finally, 8.2 g of formaldehyde (38%) was added at one time. The reaction was conducted for 6 hrs. at a stirring rate of 360 rotations/revolutions per minute (r/min) and at the normal pressure. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of butyl phenylcarbamate was 98.1% and the selectivity of polymethylene polyphenyl polycarbamate was 95.0%, wherein the selectivity of methylene diphenyl di(butyl carbamate) was 72.1%, the selectivity of trimethylene polyphenyl poly(butyl carbamate) was 20.4%, and the selectivity of tetramethylene polyphenyl poly(butyl carbamate) was 2.1%. The temperature of the oil phase product was decreased to 60° C. A majority of dimethylene polyphenyl poly(butyl carbamate) (i.e. methylene diphenyl di(butyl carbamate)) was separated in the form of crystal and filtered to obtain the target product.

Example 3

500.0 g of ethyl phenylcarbamate was dissolved in 10 L of diisooctyl sebacate and then poured into a 20 L premixed tank to be mixed. Thereafter, a 15 L aqueous phosphoric acid solution with a concentration of 40% was formulated in another 20 L premixed tank and fully mixed with 200 g of formaldehyde solution. The above solutions were continuously transported through a feeding pump to a super-gravity reactor with a volume of 30 L and subjected to the circulation reaction for 4 hrs. The reaction temperature was 100° C., the temperature pressure was 0.15 MPa and the heating was performed by a thermal conduction oil. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of ethyl phenylcarbamate was 99.5% and the selectivity of polymethylene polyphenyl poly(ethyl carbamate) was 92.6%, wherein the selectivity of methylene diphenyl di(ethyl carbamate) was 58.2%, the selectivity of trimethylene polyphenyl poly(ethyl carbamate) was 30.6%, and the selectivity of tetramethylene polyphenyl poly(ethyl carbamate) was 4.2%. The temperature of the oil phase product was decreased to 20° C. 26% of dimethylene polyphenyl poly (ethyl carbamate) (i.e., methylene diphenyl di(ethyl carbamate)) was separated in the form of crystal and filtered to obtain the target product.

Example 4

1000.0 g of ethyl phenylcarbamate was weighted and dissolved in 50 L of naphthenic oil to be fully mixed. 50 L of aqueous sulfuric acid solution with a concentration of 60% was fully mixed with 200 g of paraformaldehyde (mixed polymers) solid. The above solutions were continuously transported through a feeding pump to a tube reactor with a diameter of 50 mm and subjected to the circulation reaction for 4 hrs. The reaction temperature was 180° C., the pressure was about 3.50 MPa and the heating was performed by a thermal conduction oil. After the reaction was complete, a mixture of liquid phase products was collected and allowed to stand still and stratify and subjected to the oil water separation while it was hot. Each of the oil phase and the aqueous phase was then sampled at a certain mass for high performance liquid chromatography analysis. As a result, the conversion of ethyl phenylcarbamate was 98.5% and the selectivity of polymethylene polyphenyl poly(ethyl carbamate) was 91.6%, wherein the selectivity of methylene diphenyl di(ethyl carbamate) was 54.2%. The temperature of the oil phase product was decreased to 100° C. 29% of dimethylene polyphenyl poly(ethyl carbamate) (i.e., methylene diphenyl di(ethyl carbamate)) was separated in the form of crystal and filtered to obtain the target product.

Example 5

20.2 g of propyl phenylcarbamate was dissolved in 100 ml of o-dichlorobenzene. The solution was then poured into a 500 ml three-necked flask. The three-necked flask was then further charged with 200 ml of 20% sulfuric acid and placed into an oil bath to be heated to 90° C. Finally, 20 g of formaldehyde (10%) was dropwisely added at a constant rate. The reaction was conducted for 2 hrs. at a stirring rate of 360 r/min and at the normal pressure. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 58.35% and the selectivity of polymethylene polyphenyl poly(propyl carbamate) was 90.6%, wherein the selectivity of methylene diphenyl di(propyl carbamate) was 79.8%, the selectivity of trimethylene polyphenyl poly(propyl carbamate) was 9.4%, and the selectivity of tetramethylene polyphenyl poly(propyl carbamate) was 0.2%. The temperature of the oil phase product was decreased to 50° C. A majority of dimethylene polyphenyl poly(propyl carbamate) (i.e., methylene diphenyl di(propyl carbamate)) was separated in the form of crystal and filtered to obtain the target product.

Example 6

9.57 g of propyl phenylcarbamate was weighted and dissolved in 100 ml of chlorobenzene. The solution was then poured into a 500 ml three-necked flask. The three-necked flask was then further charged with 200 ml of 60% formic acid and placed into an oil bath to be heated to 90° C. Finally, 10 g of formaldehyde (38%) was added at one time. The reaction was conducted for 180 min at a stirring rate of 600 r/min and at a pressure of 0.15 MPa. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 60% and the selectivity of polymethylene polyphenyl poly(propyl carbamate) was 97.6%, wherein the selectivity of methylene diphenyl di(propyl carbamate) was 90.0%, and the selectivity of trimethylene polyphenyl poly(propyl carbamate) was 7.6%. The temperature of the oil phase product was decreased to 20° C. 97% of dimethylene polyphenyl poly(propyl carbamate) (i.e., methylene diphenyl di(propyl carbamate)) was separated in the form of crystal and filtered to obtain the target product.

Example 7

10.5 g of propyl phenylcarbamate was dissolved in 100 ml of n-pentane. The solution was then poured into a 500 ml three-necked flask. Then, the three-necked flask was further charged with 200 ml of 40% sulfuric acid and subsequently placed into an oil bath to be heated to 60° C. Finally, 3 g of trioxymethylene was added at one time. The reaction was conducted for 120 min. at a stirring rate of 600 r/min and at the normal pressure. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 25.34% and the selectivity of polymethylene polyphenyl poly(propyl carbamate) was 99.2%, wherein the selectivity of methylene diphenyl di(propyl carbamate) was 96.8%, and the selectivity of trimethylene polyphenyl poly(propyl carbamate) was 2.4%. The temperature of the oil phase product was decreased to 40° C. 20% of methylene diphenyl di(propyl carbamate was separated in the form of crystal and filtered to obtain the target product.

Example 8

10.02 g of propyl phenylcarbamate was dissolved in 100 ml of cyclohexane. The solution was then poured into a 500 ml three-necked flask. Then, the three-necked flask was further charged with 200 ml of 40% sulfuric acid, nanometer zinc oxide promoter at a mass fraction of 2% and 10.8 g of formaldehyde (38%) added at one time and subsequently placed into an oil bath to be heated to 140° C. The reaction was conducted for 10 min. at a stirring rate of 600 r/min and at a pressure of about 2.0 MPa. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 98.8% and the selectivity of polymethylene polyphenyl poly(propyl carbamate) was 90.4%, wherein the selectivity of methylene diphenyl di(propyl carbamate) was 56.8%, the selectivity of trimethylene polyphenyl poly(propyl carbamate) was 29.3% and the selectivity of tetramethylene polyphenyl poly(propyl carbamate)

was 4.1%. The temperature of the oil phase product was decreased to 40° C. A minority of methylene diphenyl di(propyl carbamate) was separated in the form of crystal and filtered to obtain the target product.

Example 9

20.02 g of propyl phenylcarbamate was dissolved in 100 ml of o-dichlorobenzene. The solution was then poured into a 500 ml three-necked flask. Then, the three-necked flask was further charged with 200 ml of 40% sulfuric acid and subsequently placed into an oil bath to be heated to 90° C. Finally, 5.5 g of formaldehyde (38%) was added at one time. The reaction was conducted for 120 min. at a stirring rate of 360 r/min and at a pressure of 0.15 MPa. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 73.7% and the selectivity of polymethylene polyphenyl poly(propyl carbamate) was 96.4%, wherein the selectivity of methylene diphenyl di(propyl carbamate) was 92.8%, and the selectivity of trimethylene polyphenyl poly(propyl carbamate) was 3.5%. The temperature of the oil phase product was decreased to 40° C. 97% of methylene diphenyl di(propyl carbamate) was separated in the form of crystal and filtered to obtain the target product.

Example 10

20.2 g of propyl phenylcarbamate was dissolved in 100 ml of o-diethylbenzene. The solution was then poured into a 500 ml three-necked flask. Then, the three-necked flask was further charged with 200 ml of 40% sulfuric acid and subsequently placed into an oil bath to be heated to 90° C. Finally, 5.5 g of formaldehyde (38%) and dibutyl tin oxide promoter with a mass fraction of 5% were added at one time. The reaction was conducted for 120 min. at a stirring rate of 360 r/min and at the normal pressure. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 74.35% and the selectivity of polymethylene polyphenyl poly(propyl carbamate) was 96.2%, wherein the selectivity of methylene diphenyl di(propyl carbamate) was 94.7%, and the selectivity of trimethylene polyphenyl poly(propyl carbamate) was 3.4%. The temperature of the oil phase product was decreased to 40° C. 97% of methylene diphenyl di(propyl carbamate) was separated in the form of crystal and filtered to obtain the target product.

Example 11

20.2 g of propyl phenylcarbamate was dissolved in 100 ml of dichloroethane. The solution was then poured into a 500 ml three-necked flask. Then, the three-necked flask was further charged with 200 ml of 30% hydrochloric acid and copper chloride promoter with a mass fraction of 10% and subsequently placed into an oil bath to be heated to 80° C. Finally, 5.5 g of formaldehyde (38%) was dropwisely added at a constant rate. The reaction was conducted for 120 min. at a stirring rate of 360 r/min and at the normal pressure. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 82.8% and the selectivity of polymethylene polyphenyl poly(propyl carbamate) was 98.2%, wherein the selectivity of methylene diphenyl di(propyl carbamate) was 90.08%, and the selectivity of trimethylene polyphenyl poly(propyl carbamate) was 7.9%. The temperature of the oil phase product was decreased to 40° C. A majority of methylene diphenyl di(propyl carbamate) was separated in the form of crystal and filtered to obtain the target product.

Example 12

20.02 g of propyl phenylcarbamate was weighted and dissolved in 100 ml of chlorobenzene. The solution was then poured into a 500 ml three-necked flask. The three-necked flask was then further charged with 200 ml of 40% sulfuric acid (260 g) and about 1% by mass of sodium chloride (aid) and subsequently placed into an oil bath to be heated to 90° C. Finally, 20 g of formaldehyde (10%) was dropwisely added at a constant rate. The reaction was conducted for 120 min. at a stirring rate of 360 r/min and at a pressure of 0.20 MPa. After the reaction was complete, the stirring was stopped and the solution was allowed to stand still and stratify and subjected to the oil water separation while it was hot. Each of the oil phase and the aqueous phase was then sampled at a certain mass for high performance liquid chromatography analysis. As a result, the conversion of propyl phenylcarbamate was 71.35% and the selectivity of polymethylene polyphenyl poly(propyl carbamate) was 97.2%, wherein the selectivity of methylene diphenyl di(propyl carbamate) was 94.1%, and the selectivity of trimethylene polyphenyl poly(propyl carbamate) was 3%. The temperature of the oil phase product was decreased to 40° C. A majority of methylene diphenyl di(propyl carbamate) was separated in the form of crystal and filtered to obtain the target product.

What is claimed is:

1. A method for preparing polymethylene polyphenyl polycarbamate that is carried out through a condensation of phenylcarbamate with a methylating reagent under a catalyzation of a phase transfer acid catalyst, comprising the steps of:
   a) dissolving phenylcarbamate in a water-immiscible organic solvent to form a solution A;
   b) formulating an aqueous acid catalyst solution to form a solution B;
   c) forming a reaction system comprising an organic phase and an aqueous phase by firstly adding a methylating reagent to the solution B and then mixing the solution A and the solution B, or by adding the methylating reagent at the same time of mixing the solution A and the solution B or after mixing the solution A and the solution B, wherein the organic phase comprises phenylcarbamate and the aqueous phase comprises the phase transfer acid catalyst and the methylating reagent;
   d) reacting the reaction system under stirring at a reaction temperature of about 30° C. to about 200° C. and a reaction pressure of about 0.05 MPa to about 5 MPa to produce a polymethylene polyphenyl polycarbamate product mixture dissolved in the organic phase; and
   e) separating the polymethylene polyphenyl polycarbamate product mixture by allowing the organic phase and the aqueous phase to stand still and stratify.

2. The method according to claim 1, wherein the method further comprises the step of:
f) crystallizing the polymethylene polyphenyl polycarbamate product mixture by decreasing the temperature thereof so as to separate methylene diphenyl dicarbamate therefrom.

3. The method according to claim 1, wherein the water-immiscible organic solvent in the step a is selected from linear alkylanes, cyclic alkanes, naphthenic oils, halogenated hydrocarbons, aromatic hydrocarbons, esters and a combination thereof.

4. The method according to claim 1, wherein in the step a, a mass concentration of phenylcarbamate in the solution A is about 1% to about 90%.

5. The method according to claim 1, wherein the aqueous acid catalyst solution in the step b is sulfuric acid, nitric acid, hydrochloric acid, phosphoric acid, boric acid, formic acid, acetic acid, butyric acid or a mixture thereof.

6. The method according to claim 1, wherein a mass fraction of an acid catalyst in the aqueous acid catalyst solution is about 5% to about 80%.

7. The method according to claim 1, wherein a promoter is added to the aqueous acid catalyst solution in the step b.

8. The method according to claim 7, wherein the promoter is sodium chloride, copper chloride, dibutyl tin oxide, or nanometer zinc oxide, and a mass concentration of the promoter in the aqueous acid catalyst solution is about 0.01% to about 20%.

9. The method according to claim 1, wherein the methylating reagent in the step c is selected from formaldehyde, paraformaldehyde, or a combination thereof.

10. The method according to claim 1, wherein the reaction in the step d is conducted in a reactor selected from one of a tubular reactor, a tower reactor, a tank reactor, a jet reactor, a moving bed reactor and a super-gravity reactor, or a combination of two thereof.

11. The method according to claim 1, wherein a volume ratio of the organic phase to the aqueous phase in the reaction system is between about 0.1 and about 100.

12. The method according to claim 1, wherein a molar ratio of the methylating reagent to phenylcarbamate in the reaction system is about 0.05 to about 10.0.

13. The method according to claim 1, wherein the reaction temperature is about 60° C. to about 120° C., the reaction pressure is about 0.1 MPa to about 1.0 MPa, and a reaction time is about 1 minute to about 480 minutes.

14. The method according to claim 2, wherein a temperature for the temperature-decreasing crystallization is about 20° C. to about 100° C.

15. The method according to claim 1, wherein a mass concentration of the polymethylene polyphenyl polycarbamate product mixture in the organic phase is about 1% to about 80%.

16. The method according to claim 2, wherein the temperature for the temperature-decreasing crystallization is 20° C. to 100° C.

17. The method according to claim 1, wherein the mass concentration of the polymethylene polyphenyl polycarbamate product mixture in the organic phase is 1% to 80%.

* * * * *